US007682352B2

(12) United States Patent
Rafiee et al.

(10) Patent No.: US 7,682,352 B2
(45) Date of Patent: Mar. 23, 2010

(54) CATHETER WITH CURVED DISTAL SECTION HAVING REINFORCING STRIP AND METHOD OF MAKING SAME

(75) Inventors: Nasser Rafiee, Andover, MA (US); Nareak Douk, Lowell, MA (US); Peter Strickler, Tewksbury, MA (US); Matthew S. Poole, Bradford, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 384 days.

(21) Appl. No.: 10/952,996

(22) Filed: Sep. 28, 2004

(65) Prior Publication Data

US 2006/0074308 A1     Apr. 6, 2006

(51) Int. Cl.
*A61M 25/00* (2006.01)

(52) U.S. Cl. .................. 604/532; 604/524; 604/525; 604/530

(58) Field of Classification Search .............. 604/523, 604/524, 525, 526, 532, 529, 530; 600/435; 606/108
See application file for complete search history.

(56) References Cited

U.S. PATENT DOCUMENTS

| | | | | |
|---|---|---|---|---|
| 3,890,977 A * | 6/1975 | Wilson | ............... | 604/531 |
| 4,822,345 A * | 4/1989 | Danforth | ............... | 604/524 |
| 4,909,787 A * | 3/1990 | Danforth | ............... | 604/95.03 |
| 5,176,660 A * | 1/1993 | Truckai | ............... | 604/527 |
| 5,334,168 A | 8/1994 | Hemmer | | |
| 5,368,564 A * | 11/1994 | Savage | ............... | 604/95.04 |
| 5,451,209 A | 9/1995 | Ainsworth et al. | | |
| 5,453,099 A * | 9/1995 | Lee et al. | ............... | 604/524 |
| 5,531,685 A | 7/1996 | Hemmer et al. | | |
| 5,702,373 A | 12/1997 | Samson | | |
| 5,722,425 A | 3/1998 | Bostrom | | |
| 5,792,124 A * | 8/1998 | Horrigan et al. | ............... | 604/525 |
| 5,827,242 A | 10/1998 | Follmer et al. | | |
| 5,836,926 A * | 11/1998 | Peterson et al. | ............... | 604/527 |
| 5,876,385 A * | 3/1999 | Ikari et al. | ............... | 604/523 |
| 5,902,287 A * | 5/1999 | Martin | ............... | 604/532 |
| 5,916,178 A | 6/1999 | Noone et al. | | |
| 5,971,975 A * | 10/1999 | Mills et al. | ............... | 604/527 |
| 6,059,769 A * | 5/2000 | Lunn et al. | ............... | 604/523 |
| 6,077,258 A * | 6/2000 | Lange et al. | ............... | 604/527 |
| 6,096,036 A | 8/2000 | Bowe et al. | | |
| 6,185,449 B1 | 2/2001 | Berg et al. | | |
| 6,199,262 B1 * | 3/2001 | Martin | ............... | 29/525.15 |
| 6,217,566 B1 | 4/2001 | Ju et al. | | |
| 6,251,092 B1 * | 6/2001 | Qin et al. | ............... | 604/95.01 |
| 6,254,550 B1 | 7/2001 | McNamara et al. | | |
| 6,408,214 B1 | 6/2002 | Williams et al. | | |
| 6,503,353 B1 * | 1/2003 | Peterson et al. | ............... | 156/86 |
| 6,567,704 B2 * | 5/2003 | Sundquist et al. | ............... | 607/119 |
| 6,569,150 B2 * | 5/2003 | Teague et al. | ............... | 604/524 |
| 6,598,280 B1 * | 7/2003 | Giba et al. | ............... | 29/447 |
| 6,652,508 B2 * | 11/2003 | Griffin et al. | ............... | 604/526 |
| 6,852,261 B2 * | 2/2005 | Benjamin | ............... | 264/248 |
| 6,988,007 B1 * | 1/2006 | Morgan et al. | ............... | 607/123 |
| 2001/0027310 A1 * | 10/2001 | Parisi et al. | ............... | 604/524 |
| 2002/0107506 A1 * | 8/2002 | McGuckin et al. | ............... | 604/523 |

* cited by examiner

*Primary Examiner*—Nicholas D Lucchesi
*Assistant Examiner*—Laura A Bouchelle

(57) ABSTRACT

A catheter having an elongate hollow shaft with a curved distal section having at least one pre-curved reinforcing strip embedded therein. The pre-curved reinforcing strip comprises a relatively stiff material that is unaffected by the process of thermoforming a final curve in the catheter. Methods of making the catheter are also described.

13 Claims, 4 Drawing Sheets

CATHETER WITH CURVED DISTAL SECTION HAVING REINFORCING STRIP AND METHOD OF MAKING SAME

FIELD OF THE INVENTION

The present invention relates generally to medical devices. More particularly, the invention relates to a curved catheter, the curved portion of the catheter having a reinforcing strip.

BACKGROUND OF THE INVENTION

Catheters are used for myriad medical procedures and applications, such as in the treatment of a wide variety of vascular disorders. Catheters generally comprise an elongated shaft having at least one lumen therethrough and are inserted into a patient's body percutaneously or via natural orifices. Typically, a cardiovascular catheter is inserted percutaneously, and then advanced through the patient's vasculature to a site targeted for treatment.

A vascular catheter is typically flexible, yet sufficiently stiff so as to resist kinking while being pushed through the patient's vasculature, over a guidewire, or through a lumen of another catheter. A curved interventional guiding catheter or angiography catheter has preformed bends to locate and direct the tip of the catheter in a vessel during advancement of a treatment device, or injection of x-ray contrast media through the catheter. However, the preformed bends need to be sufficiently elastic to allow the curved portion of the catheter to be temporarily, substantially straightened while the catheter is passed through the patient's vessels until it reaches the intended position.

Typically, curved vascular catheters are initially assembled in a straight configuration and include one or more thermoplastic components. The straight catheter is deformed into a desired curve shape using tools such as an external mold or, more commonly, by inserting a stiff forming mandrel into the lumen of the catheter. To form or set the catheter in the shape of the mold or mandrel, the assembly is heated above the glass transition temperature $T_g$ of one or more thermoplastic component(s). However, the catheter distal region that is to be curved may further comprise components that resist thermoforming at the curve-setting temperature used. These "unformable" components may be non-thermoplastic elements such as a metallic braid reinforcement layer or a tubular liner of non melt-extrudable fluoropolymer, such as polytetrafluoroethylene (PTFE). Another "unformable" component may be a thermoplastic element, such as a low-friction tubular liner having a glass transition temperature $T_g$ above the curve setting temperature used to shape the catheter. Such "unformable" components tend to retain the original straight configuration of the catheter, thus resisting the curve shape that is heat set into the "formable" thermoplastic component(s).

Improvements in design and materials have allowed curved catheters to be constructed with increasingly thinner walls, which offer advantages such as reduced overall catheter diameter and/or increased lumen size. However, such thin walls also incur correspondingly reduced amounts of the "formable" thermoplastic components that are relied upon to overcome the inherent straightness of the "unformable" components to effectively retain the catheter's desired curve shape. Therefore, during use, the pre-curved distal region of the catheter too often tends to unbend and/or back out from the entrance of a vessel in which it was positioned. Thus, a need exists for a curved catheter having localized reinforcement of the pre-curved shape. Such reinforcement should provide the curve shape with greater stiffness while still permitting elastic straightening of the curve shape during placement. Other desirable features and characteristics of the present invention will become apparent from the subsequent detailed description and the appended claims taken in conjunction with the accompanying drawings.

BRIEF SUMMARY OF THE INVENTION

The invention provides a catheter having lumen extending there through, a curved distal section, and including a first thermoplastic material. One or more pre-curved reinforcing strips are positioned in the curved distal section to aid in curve retention. The pre-curved reinforcing strips are made of a material having a higher heat setting temperature than the first thermoplastic material. The material of the pre-curved reinforcing strips may be stiffer than the first thermoplastic material. The material of the pre-curved reinforcing strips may be a second thermoplastic material.

In other embodiments of the invention, the catheter may also include the pre-curved reinforcing strip being positioned in an outer curved portion of the curved distal section and/or in an inner curved portion of the curved distal section. The pre-curved reinforcing strip may also be a plurality of pre-curved reinforcing strips that are spaced apart longitudinally, circumferentially, or both. The pre-curved reinforcing strip may comprise a shape memory material such as nitinol. The flexible tubing may be multilayered tubing, with an inner layer, an outer layer, and a reinforcement layer disposed there between. The pre-curved reinforcing strip may be positioned between the reinforcement layer and the outer layer in the curved distal section.

According to another aspect of the present invention, a method is disclosed for constructing a catheter from flexible tubing comprising an inner layer, an outer layer, and a reinforcement layer embedded there between. The method includes removing material from a segment of the outer layer to form an annular groove in the distal shaft section. A pre-curved reinforcing strip is placed in the annular groove and is covered with a thermoplastic material, which fills the groove. The distal shaft section is formed into a curve shape that is similar to the shape of the pre-curved reinforcing strip.

BRIEF DESCRIPTION OF THE DRAWINGS

The following drawings are illustrative of the particular embodiments of the invention and therefore do not limit its scope. They are presented to assist in providing a proper understanding of the invention. The drawings are not to scale and are intended for use in conjunction with the explanations in the following detailed descriptions. The present invention will hereinafter be described in conjunction with the appended drawings, wherein like reference numerals denote like elements, and.

DETAILED DESCRIPTION OF THE INVENTION

The following detailed description is merely exemplary in nature and is not intended to limit the invention or the application and uses of the invention. Additionally, although the catheter is described herein as a guiding catheter, it will be appreciated that the principals of the invention can be applied to any other type of curved catheter. Furthermore, there is no intention to be bound by any expressed or implied theory presented in the preceding technical field, background, brief summary or the following detailed description.

Figure 1:
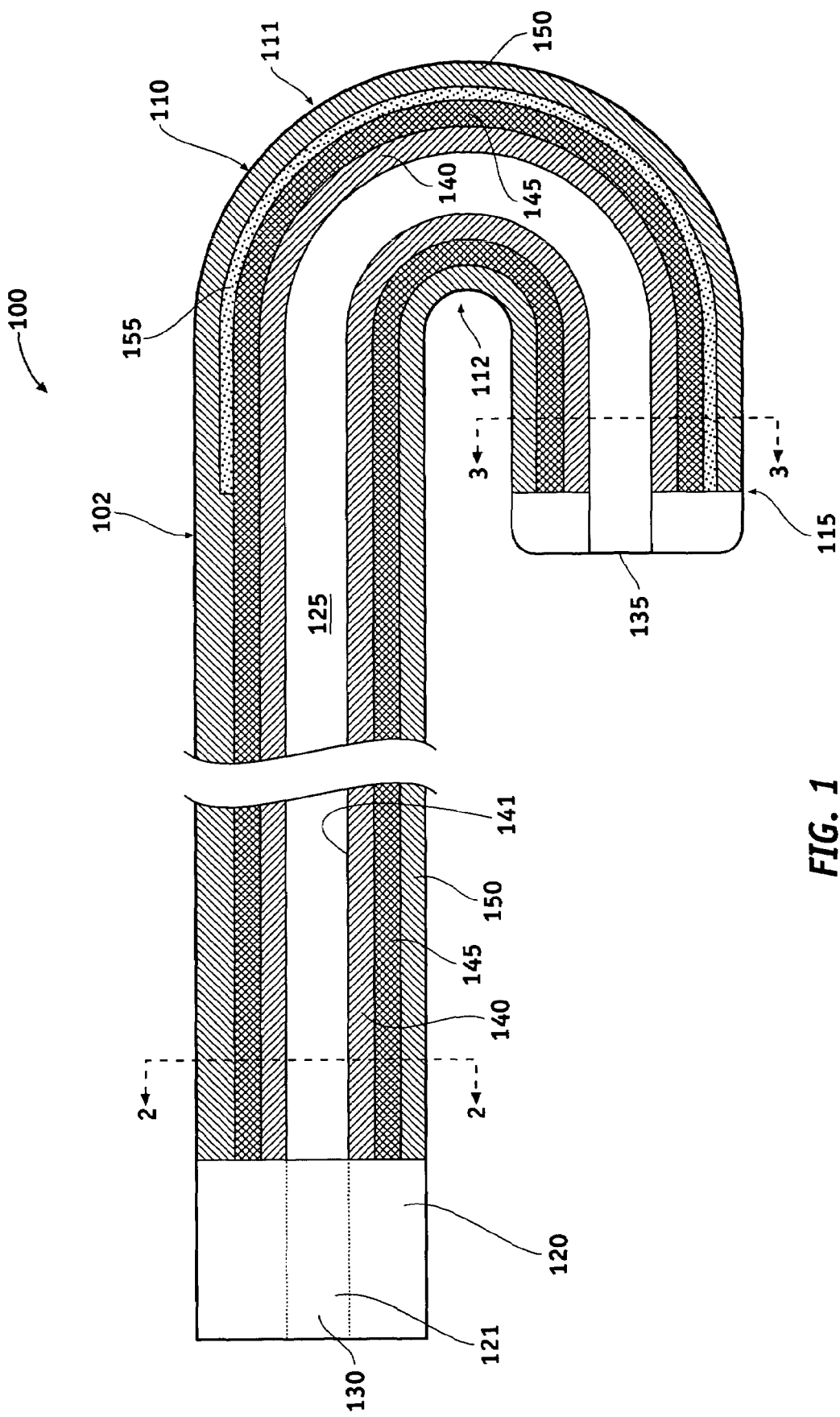
FIG. 1 is a longitudinal cross-sectional view showing one embodiment of a catheter in accordance with the invention.

FIG. 1 shows guiding catheter 100 including elongate shaft 102 with curved distal shaft section 110, soft distal end 115, and proximal hub 120. Catheter 100 also has lumen 125 extending there through from proximal opening 130 to distal opening 135. Catheter 100 is constructed to have sufficient stiffness, in axial bending and in torsion, to advance through a patient's vasculature to distant arterial locations without buckling or undesirable bending. To achieve these characteristics, shaft 102 may be constructed with multiple layers, including inner layer 140, reinforcement layer 145 and outer layer 150.

Figure 2:
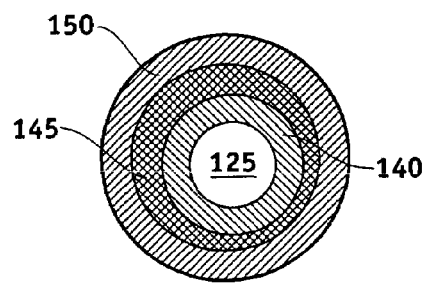
FIG. 2 is a transverse cross-section view of the catheter of FIG. 1 taken along line 2-2.

In the embodiment shown in FIGS. 1 and 2, inner layer 140 is a tubular single layer of a biocompatible material, such as polyamide, polyester, polytetrafluoroethylene (PTFE), polyethylene, polypropylene, polyurethane, or PEBAX® polyethylene block amide copolymer, which is available from ELF Atochem, Philadelphia, Pa., U.S.A. Inner layer 140 is sized and shaped to form hollow lumen 125 for receiving a guidewire and/or a therapeutic device, such as a balloon catheter. Inside surface 141 of inner layer 140 may have a slippery coating to reduce frictional forces between surface 141 and a therapeutic device. In other embodiments, inner layer 140 may be a multi-layer design wherein only a first layer adjacent lumen 125 is a low-friction material.

Reinforcement layer 145 is sandwiched between inner layer 140 and outer layer 150 to enhance torsional strength and to inhibit kinking of catheter 100 during advancement through the patient's vasculature. Reinforcement layer 145 may comprise braided high-strength polymer filaments or metal wires. Outer layer 150 may be formed over reinforcement layer 145 via any known method, such as over-extrusion, pultrusion or compression molding of an oversized tubular segment using heat shrink tubing as a removable tool. Outer layer 150 may be bonded to inner layer 140 through the interstices between the filaments of reinforcement layer 145 using thermal bonding, or an adhesive or a thermoplastic tie layer. Outer layer 150 may comprise a thermoplastic polymer such as polyamide, polyester, polyethylene, polypropylene, polyurethane, or PEBAX®. Outer layer 150 may be formed of a thermoplastic material selected to have a glass transition temperature $T_g$ that is heat formable into a curved distal portion, as will be described below. Those skilled in the art will understand that elongate shaft 102 may include more or fewer layers than those disclosed herein, while still meeting the desired results.

To prevent injury to the patient's vessels, catheter 100 may include soft distal end 115 coupled to distal shaft section 110. Hub 120 is a conventional catheter fitting coupled to the proximal end of elongate shaft 102. Those of skill in the art know numerous materials and methods of forming and attaching soft distal end 115 and hub 120.

FIG. 1 illustrates distal shaft section 110 with a pre-formed curved shape comprising outer curved portion 111 and inner curved portion 112. For simplicity of illustration, distal shaft section 110 is shown with only a single U-shaped bend. The invention may also be practiced with catheter curves having multiple bends, including, but not limited to, any of the myriad catheter curve shapes known from specialties such as cardiology, radiology and neuroradiology.

Figure 3:
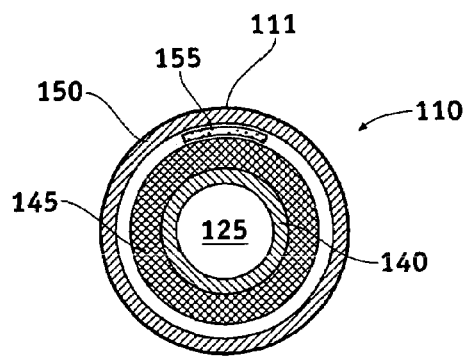
FIG. 3 is a transverse cross-sectional view of the catheter of FIG. 1 taken along line 3-3.

To help retain the catheter curve shape during use, distal shaft section 110 has one or more embedded, pre-curved reinforcing strips 155. As used herein, the terms embedded and embedment refer to reinforcing strips 155 being encapsulated and restrained within the wall of catheter 100. In the embodiment shown in FIGS. 1 and 3, pre-curved reinforcing strip 155 is embedded in outer curved portion 111 between reinforcement layer 145 and outer layer 150. Reinforcing strip 155 is pre-curved prior to embedment and is made of a material that is stiffer than surrounding thermoplastic portions of catheter 100, as measured by the modulus of elasticity, also called Young's modulus. The pre-formed shape and relatively high modulus of reinforcing strip 155 provides additional support to the curved thermoplastic component(s) in distal shaft section 110, and can aid in overcoming the inherent straightness of any unformable catheter component(s) discussed above.

Figure 8:
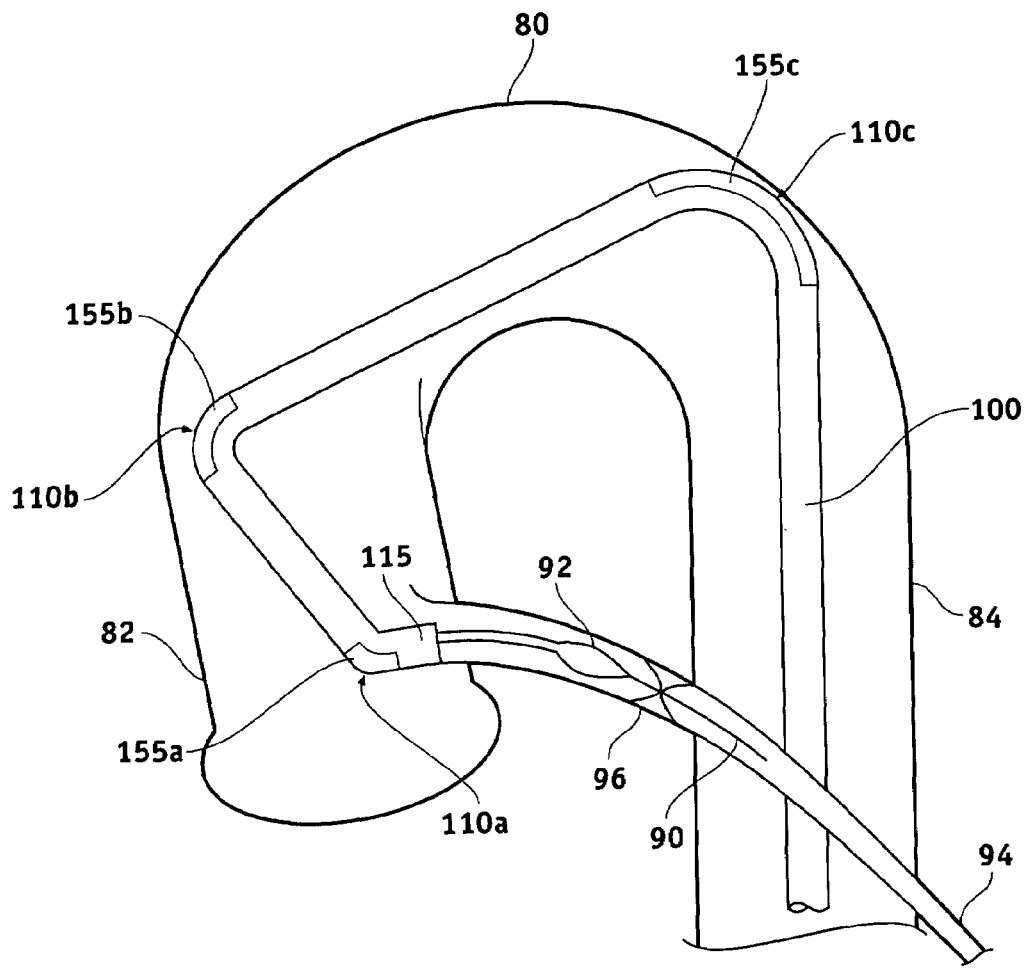
FIG. 8 is a longitudinal cross-sectional view showing an additional embodiment of the catheter in accordance with the invention.

Before reinforcing strip 155 is embedded between reinforcement layer 145 and outer layer 150, all or a portion of reinforcing strip 155 is pre-curved to approximate one or more intended final curves in distal shaft section 110. Reinforcing strip 155 may be relatively short in length and may be pre-curved to reinforce only one of several bends in a catheter curve shape, although several strips may be longitudinally spaced to reinforce a series of bends, as shown in FIG. 8. Alternatively, reinforcing strip 155 may be elongate and may have several bends to match and extend along a complex curve shape. In another embodiment, the one or more preformed bends in reinforcing strip 155 may have tighter radii than the final curves of distal shaft section 110 with which they will be aligned. A tighter radius bend in reinforcing strip 155 will provide additional reinforcement of the catheter curve in which it is embedded.

Figure 4:
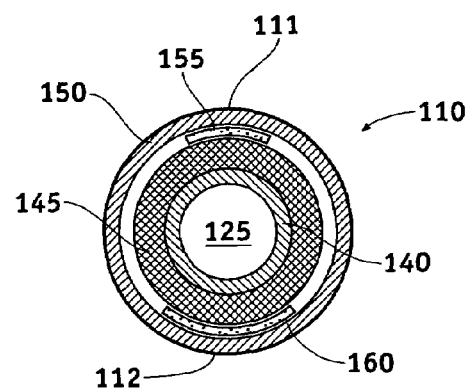
FIGS. 4-7 are transverse cross-sectional views showing additional embodiments of the catheter in accordance with the invention.
Figure 5:
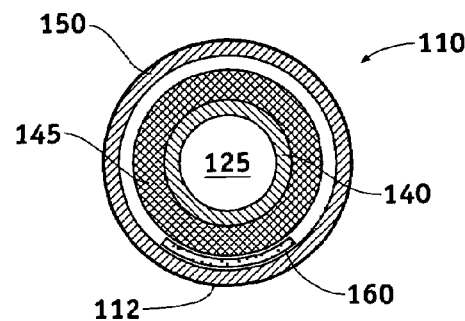

Additional embodiments for the number and placement of pre-curved reinforcing strips are shown in FIGS. 4-7. FIG. 4 illustrates an embodiment in which pre-curved reinforcing strip 155 embedded in outer curved portion 111 and pre-curved reinforcing strip 160 embedded in inner curve portion 112. FIG. 5 shows an embodiment in which only inner pre-curved reinforcing strip 160 is embedded at inner curve 112 of distal shaft section 110.

Figure 6:
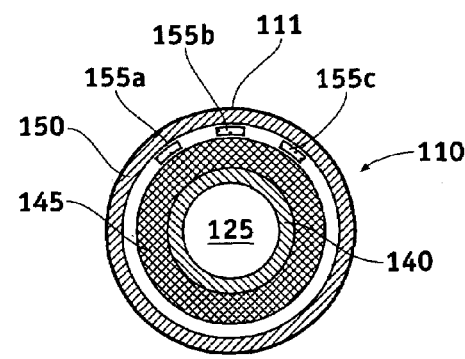
Figure 7:
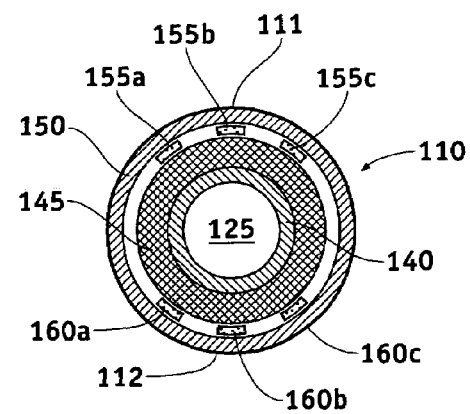

A plurality of pre-curved reinforcing strips may be disposed spaced apart from each other, either longitudinally or circumferentially. For example, FIG. 6 shows an embodiment wherein pre-curved reinforcing strips 155a, 155b, and 155c are embedded in outer curved portion 111 of distal shaft section 110. Those skilled in the art will recognize that more or fewer pre-curved reinforcing strips may be used and their spacing may be varied to achieve the desired results. In the embodiment shown in FIG. 7, a plurality of second pre-curved reinforcing strips 160a, 160b and 160c are embedded in inner curved portion 112 and pre-curved reinforcing strips 155a, 155b and 155c are embedded in outer curved portion 111. In other embodiments, inner pre-curved reinforcing strips 160a, 160b and 160c may be used alone, similar to FIG. 5. In still other embodiments, the pre-curved reinforcing strips may be positioned on the side of the catheter shaft (not shown). All embodiments are shown with reinforcing strips 155 sandwiched between reinforcement layer 145 and outer layer 150. However, those of skill in the art will recognize that, although the embodiment(s) would be more difficult to manufacture, reinforcing strips 155 could be effectively sandwiched between reinforcement layer 145 and inner layer 140.

In one embodiment, high-modulus pre-curved reinforcing strip 155 may be made of metal, such as stainless steel, cobalt nickel superalloy, or "superelastic" metal, i.e. stress-induced-martensite nitinol (TiNi). In another embodiment, reinforcing strip 155 may be cast or machined in the desired curve shape from a rigid thermoset polymer, such as polyimide or epoxy. Reinforcing strip 155 may also be extruded and thermoformed, or injection molded directly into the desired curve shape from a high-modulus thermoplastic polymer. Both thermoset polymers and thermoplastic polymers can incorporate stiffening fillers.

Reinforcing strip 155 is formed into a desired curve shape prior to embedment of reinforcing strip 155 in the catheter. This is because the temperatures required to form or change the shape of metal or thermoplastic materials of reinforcing strip 155 are higher than the curve-setting temperature for catheter 100. Therefore, if a straight, metal or thermoplastic reinforcing strip 155 were embedded in catheter 100, then using the heat set or glass transition temperature required to change the shape of reinforcing strip 155 would likely damage the adjacent thermoplastic catheter components. Furthermore, if reinforcing strip 155 is formed of a thermoset polymer, then such a cross-linked material cannot be thermally re-shaped at all. As described above, thermoplastic components, such as inner layer 140 and/or outer layer 150, are heat-formed to provide the final curve shape in catheter 100. Thermoforming of the final curve shape is performed at a curve-setting temperature that is too low to affect the pre-curved shape of reinforcing strip 155.

In one embodiment, pre-curved reinforcing strip 155 is embedded in an already curved distal shaft section 110. In another embodiment, pre-curved reinforcing strip 155 is held straight during embedment in straight distal shaft section 110, which is curved afterwards. Outer layer 150 may be a single, integral tubular element, including the section of outer layer 150 disposed within distal shaft section 110. In such an embodiment, reinforcing strip 155 is embedded or held in place prior to forming outer layer 150 over reinforcement layer 145. For example, reinforcing strip 155 can be inserted in clearance space between reinforcement layer 145 and outer layer 150 before outer layer 150 is compression molded around reinforcement layer 145. Alternatively, reinforcing strip 155 can be disposed within a section of outer layer 150 that is formed separately from the remainder of outer layer 150, as will be described below.

FIG. 8 is an illustration of an embodiment of guiding catheter 100 configured for performing percutaneous transluminal coronary angioplasty of the left main coronary artery. Although FIG. 8 illustrates a left Judkin's configuration guiding catheter, the invention is not confined to this configuration. The present guiding catheter can be applied to all configurations of guiding catheters including left and right Judkin's, Sone's, Stertzer and Amplatz configurations. Related procedures that may utilize the present guiding catheter include laser angioplasty, angioscopy or atherectomy.

Aorta 80 includes ascending portion 82 and descending portion 84. Guiding catheter 100 is manipulated up descending aorta 84 and down ascending aorta 82 so that distal end 115 is within the coronary ostium, thus permitting subsequent advancement of angioplasty guide wire 90 and balloon catheter 92 within diseased vessel 94.

Advancement of balloon catheter 92 is typically resisted by regions of stenosis 96 in diseased vessel 94. This resistance creates bending stress on guiding catheter 100, causing curved distal shaft sections 110a, 110b, 110c to deform. To prevent deformation, curved distal shaft sections 110a, 110b, 110c are constructed with pre-curved reinforcing strips 155a, 155b, 155c located along outer curved portions 111 in each of curves 110a, 110b, 110c. During use of guiding catheter 100, the pre-curved reinforcing strips 155a, 155b, 155c help guiding catheter 100 retain its shape during use.

Figure 9:
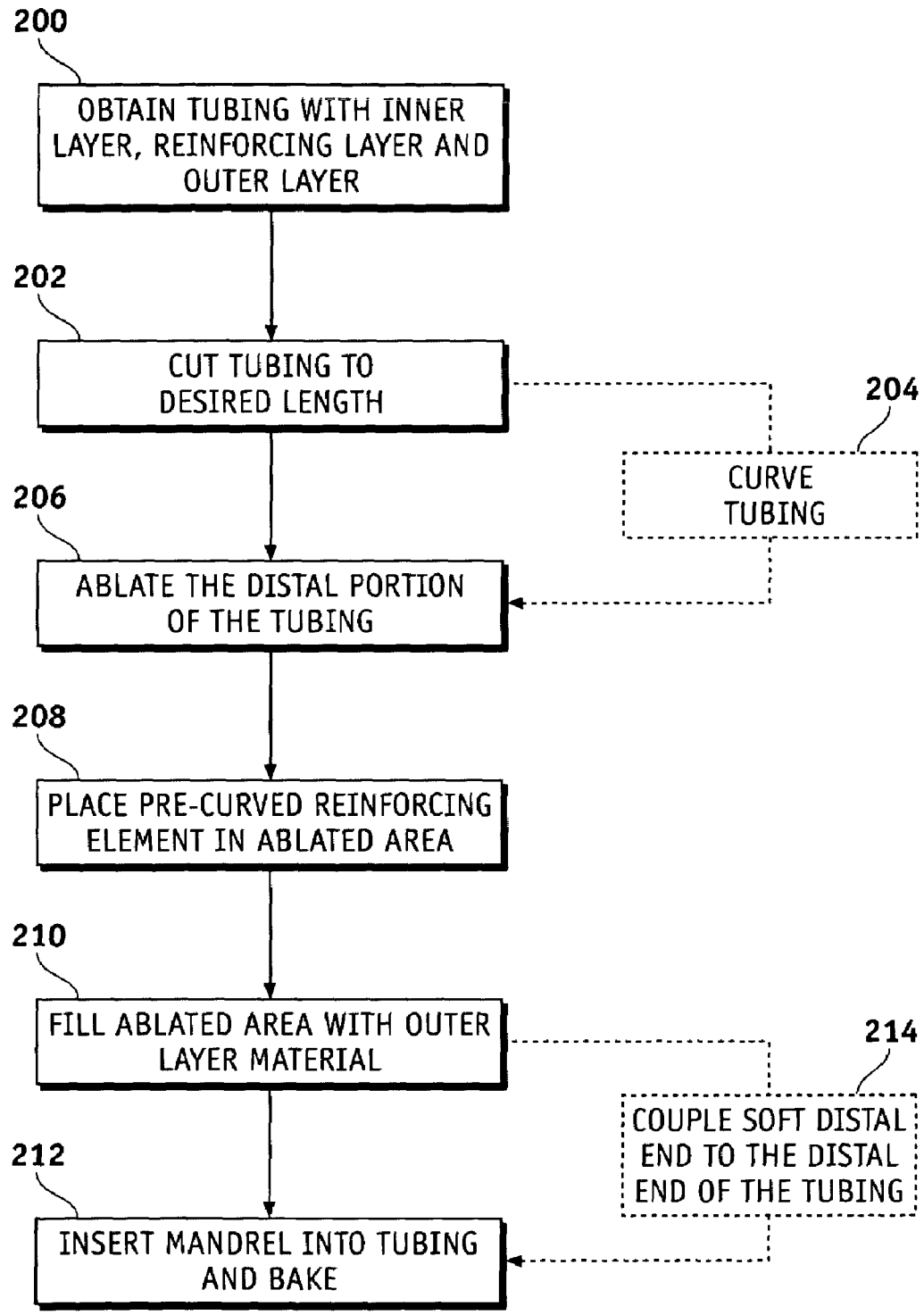
FIG. 9 is a flowchart showing a method of constructing the catheter.

FIG. 9 is a flowchart that shows one method of constructing catheter 100. First, catheter tubing having at least an inner layer, a reinforcement layer and an outer layer is provided (step 200). The tubing may be constructed by any conventional method. For example, inner layer 140 may be formed, typically by melt or paste extrusion. Inner layer 140 is then surrounded with reinforcement layer 145, as by braiding filaments directly over inner layer 140. Outer layer 150 is then formed over reinforcement layer 145, as by shrink fitting, compression molding, pultrusion or extrusion of a polymer layer over reinforcement layer 145. Then, the catheter tubing is cut or trimmed to a desired length (step 202), depending on the intended use for resulting catheter 100. For example, 100 cm is a typical finished length for coronary guiding catheters.

In one embodiment, after the tubing is cut to length, the tubing is thermally formed into a desired curve shape (step 204) using a mandrel or mold, as described previously herein. In another embodiment, the tubing is not shaped until a later step.

In the next step, a section of outer layer 150 is removed from distal shaft section 110 the catheter 100 to create an annular groove for placement of at least one reinforcing strip 155 (step 206). For example, the outer layer section can be removed by laser ablation, as described in U.S. Pat. No. 6,059,769, incorporated herein by reference.

Next, pre-curved reinforcing strip 155 is placed in the annular groove over reinforcement layer 145 (step 208). Pre-curved reinforcing strip 155 is formed of a high-modulus material in the desired shape before being placed in the groove. A polymer tube is slid over the groove and pre-curved reinforcing strip 155. The polymer tube may comprise material that is the same as or different from the material of outer layer 150. Heat shrink tubing is then fitted over the polymer tube. The parts thus assembled are heated to a temperature at or above the glass transition temperature of the polymer tube such that the shrink tubing will compression mold the polymer tube to fill the groove and to envelop pre-curved reinforcing strip 155 (step 210). Then, the heat shrink tubing is removed and the assembly is heated again to thermally shape distal shaft section 110, using either an external mold or a curved mandrel inserted into the catheter lumen (step 212). The curve of the mold or mandrel is aligned with the curve of pre-curved reinforcing strip 155. In another embodiment, soft distal end 115 is coupled to the distal end of the multilayer assembly before final curve molding (step 214).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A catheter comprising:
   an elongate shaft having open proximal and distal ends and a lumen extending therebetween, the shaft having longitudinal reinforcement to provide sufficient axial and torsional stiffness to enable the shaft to be advanced to a distal arterial location without buckling, the shaft including a thermoformed curved distal section comprising inner and outer curved portions and a first thermoplastic material, the longitudinal reinforcement extending into the curved distal section and having sufficient stiffness to apply a straightening force to the curved distal section; and a plurality of spaced apart pre-curved reinforcing strips positioned in the outer curved portion and comprising a second material that is unaffected by exposure to a glass transition temperature of the first material, the pre-curved strip and thermoformed section being configured to oppose the straightening force of the reinforcement to the curved distal section, the pre-curved strip having sufficient elasticity to enable elastic straightening of the curved shape, whereby the catheter may be navigated to the distal arterial site and whereby the distal end may return from a straightened or less curved configuration to its curved configuration under the influence of its own resilience.

2. A catheter comprising:

an elongate shaft having open proximal and distal ends and a lumen extending therebetween, the shaft having longitudinal reinforcement to provide sufficient axial and torsional stiffness to enable the shaft to be advanced to a distal arterial location without buckling, the shaft including a thermoformed curved distal section comprising inner and outer curved portions and a first thermoplastic material, the longitudinal reinforcement extending into the curved distal section and having sufficient stiffness to apply a straightening force to the curved distal section; and a plurality of spaced apart pre-curved reinforcing strips positioned in the inner curved portion and comprising a second material that is unaffected by exposure to a glass transition temperature of the first material, the pre-curved strip and thermoformed section being configured to oppose the straightening force of the reinforcement to the curved distal section, the pre-curved strip having sufficient elasticity to enable elastic straightening of the curved shape, whereby the catheter may be navigated to the distal arterial site and whereby the distal end may return from a straightened or less curved configuration to its curved configuration under the influence of its own resilience.

3. A catheter comprising:

an elongate shaft having open proximal and distal ends and a lumen extending therebetween, the shaft including a thermoformed curved distal section comprising inner and outer curved portions and a first thermoplastic material;

at least one pre-curved reinforcing strip embedded in the curved distal section and comprising a second material that is unaffected by exposure to a glass transition temperature of the first material, the pre-curved strip and thermoformed section being configured to enable elastic straightening of the curved shape, whereby the distal end may return from a straightened configuration to its curved configuration under the influence of its own resilience;

the shaft having inner and outer layers and a braided reinforcement layer disposed between the inner and outer layers; and the pre-curved reinforcing strip being embedded between the reinforcement layer and the outer layer.

4. The catheter of claim 3, wherein the pre-curved reinforcing strip comprises a material having a glass transition temperature that is higher than a glass transition temperature of the outer layer.

5. The catheter of claim 3, wherein the pre-curved reinforcing strip comprises a material having a glass transition temperature that is higher than a glass transition temperature of the inner layer.

6. The catheter of claim 3, wherein the curved distal section has an inner curved portion and an outer curved portion, the pre-curved reinforcing strip being positioned in the outer curved portion.

7. The catheter of claim 6, further comprising a second pre-curved reinforcing strip positioned in the inner curved portion.

8. The catheter of claim 3, wherein the curved distal portion has an inner curved portion and an outer curved portion, the pre-curved reinforcing strip being positioned in the inner curved portion.

9. The catheter of claim 3, wherein the pre-curved reinforcing strip comprises a material selected from a group consisting of nitinol, stainless steel, nickel cobalt superalloy, thermoset polymer, and thermoplastic polymer.

10. A method for making a curved catheter, the method comprising:

providing a tubular shaft including a distal shaft section comprising an inner layer, an outer layer, and a reinforcement layer disposed there between, the reinforcement layer having sufficient stiffness to apply a straightening force to the distal shaft section;

providing a pre-curved reinforcing strip having sufficient elasticity to enable it to be straightened and to return to its curved configuration under the influence of its resilience;

removing material from a segment of the outer layer to form an annular groove in the distal shaft section;

placing the reinforcing strip in the annular groove in an orientation to oppose the straightening force of the reinforcement layer;

covering the reinforcing strip with a thermoplastic polymer that also fills the annular groove; and subsequent to covering the reinforcing strip, thermoforming the distal shaft section to a curve shape similar to the preformed curve of the reinforcing strip.

11. The method of claim 10, wherein the pre-curved reinforcing strip is formed of a material such that the curve preformed therein is unaffected by the step of forming the distal shaft section.

12. The method of claim 10, wherein the step of covering the reinforcing strip comprises: sliding a thermoplastic tube over covering the reinforcing strip within the annular groove; fitting a heat shrink tube over the thermoplastic tube; heating the assembly to compression mold the thermoplastic tube into the groove; and removing the heat shrink tube.

13. The method of claim 10, wherein the step of forming the distal shaft section further comprises inserting a curved mandrel into the shaft and heating the assembly.

* * * * *